United States Patent [19]

Herron et al.

[11] Patent Number: 5,741,707
[45] Date of Patent: Apr. 21, 1998

[54] METHOD FOR QUANTITATIVE ANALYSIS OF EARTH SAMPLES

[75] Inventors: Michael M. Herron; Abigail Matteson, both of Ridgefield; Michael Supp, Waterbury, all of Conn.

[73] Assignee: Schlumberger Technology Corporation, Ridgefield, Conn.

[21] Appl. No.: 265,175

[22] Filed: Jun. 24, 1994

Related U.S. Application Data

[63] Continuation-in-part of Ser. No. 999,077, Dec. 31, 1992, abandoned.

[51] Int. Cl.$^6$ .................................................. G01N 33/24
[52] U.S. Cl. ........................... 436/25; 436/30; 436/31; 436/161
[58] Field of Search ............... 73/152–153; 364/422; 250/253, 255; 436/25, 30, 31, 161

[56] References Cited

U.S. PATENT DOCUMENTS

| | | | |
|---|---|---|---|
| 3,521,064 | 2/1967 | Moran et al. | 250/833 |
| 4,608,859 | 9/1986 | Rockley | 73/153 |
| 4,699,002 | 10/1987 | Rockley | 73/153 |
| 4,712,424 | 12/1987 | Herron | 73/152 |
| 4,722,220 | 2/1988 | Herron | 73/152 |
| 4,773,264 | 9/1988 | Herron | 73/152 |
| 4,839,516 | 6/1989 | Freeman et al. | 250/255 |
| 4,903,527 | 2/1990 | Herron | 73/152 |

FOREIGN PATENT DOCUMENTS

| | | | |
|---|---|---|---|
| 2 225 110 | 5/1990 | United Kingdom | G01V 3/12 |

OTHER PUBLICATIONS

Cooner et al., "Utilization of Spectrometric Information in Linked Gas Chromatography–Fourier Transform Infrared Spectroscopy–Mass Spectrometry", Anal. Chem. 1989, 61, 1571–1577.

Ruessink et al. "Quantitative Analysis of Bulk Mineralogy: The Applicability and Performance of XRD & FTIR", SPE 23828, Feb. 26–27, 1992, pp. 533–546.

Philip B. Stark et al., "Empirically minimax affine mineralogy estimates from Fourier transform infrared spectrometry using a decimated wavelet basis", *Applied Spectrocopy*, vol. 47, No. 11, pp. 1820–1829, 1993.

N.R. Draper and H. Smith, *Applied Regression Analysis*, Second Edition, John Wiley & Sons, pp. 108–117.

Frederick Mosteller and John W. Tuikey, *Data Analysis and Regression*, Addison–Wesley Publishing Co., pp. 348–379.

Abigail Matteson and Michael M. Herron, "Quantitative mineral analysis by Fourier transform infrared spectroscopy", Presented at the 1993 Society of Core Analysts Conference, Paper No. 9308.

James M. Brown and James J. Eliott, "Quantitative Analysis of Complex, Multicomponent Mixtures by FT–IR; The Analysis of Minerals and of Interacting Organic Blends", *Chemical Biological and Industrial Applications of Infrared Spectroscopy*, edited by J. Durig, Chichester: Wiley, 1985, pp. 111–128.

Paul C. Painter, Susan M. Rimmer, Randy W. Snyder, and Alan Davis, "A Fourier Transform Infrared Study of Mineral Matter in Coal: The Application of a Least Squares Curve–Fitting Program", *Applied Spectroscopy*, vol. 35, No. 1 (1981) pp. 102–106.

*Primary Examiner*—Lyle A. Alexander
*Attorney, Agent, or Firm*—Leonard W. Pojunas; Martin D. Hyden; Keith G. W. Smith

[57] ABSTRACT

A method and apparatus for analyzing a sample to determine its mineral composition. The invention combines X-ray diffraction with Fourier transform infrared spectroscopy to provide a complete spectrum including molecular vibrations, probed by FTIR scans and lattice spacing measured by X-ray diffraction in a single representation. This FX spectrum provides a more complete and accurate mineralogy than either of the techniques alone. In addition, new techniques for independent X-ray diffraction analysis and FTIR analysis are described.

16 Claims, 9 Drawing Sheets

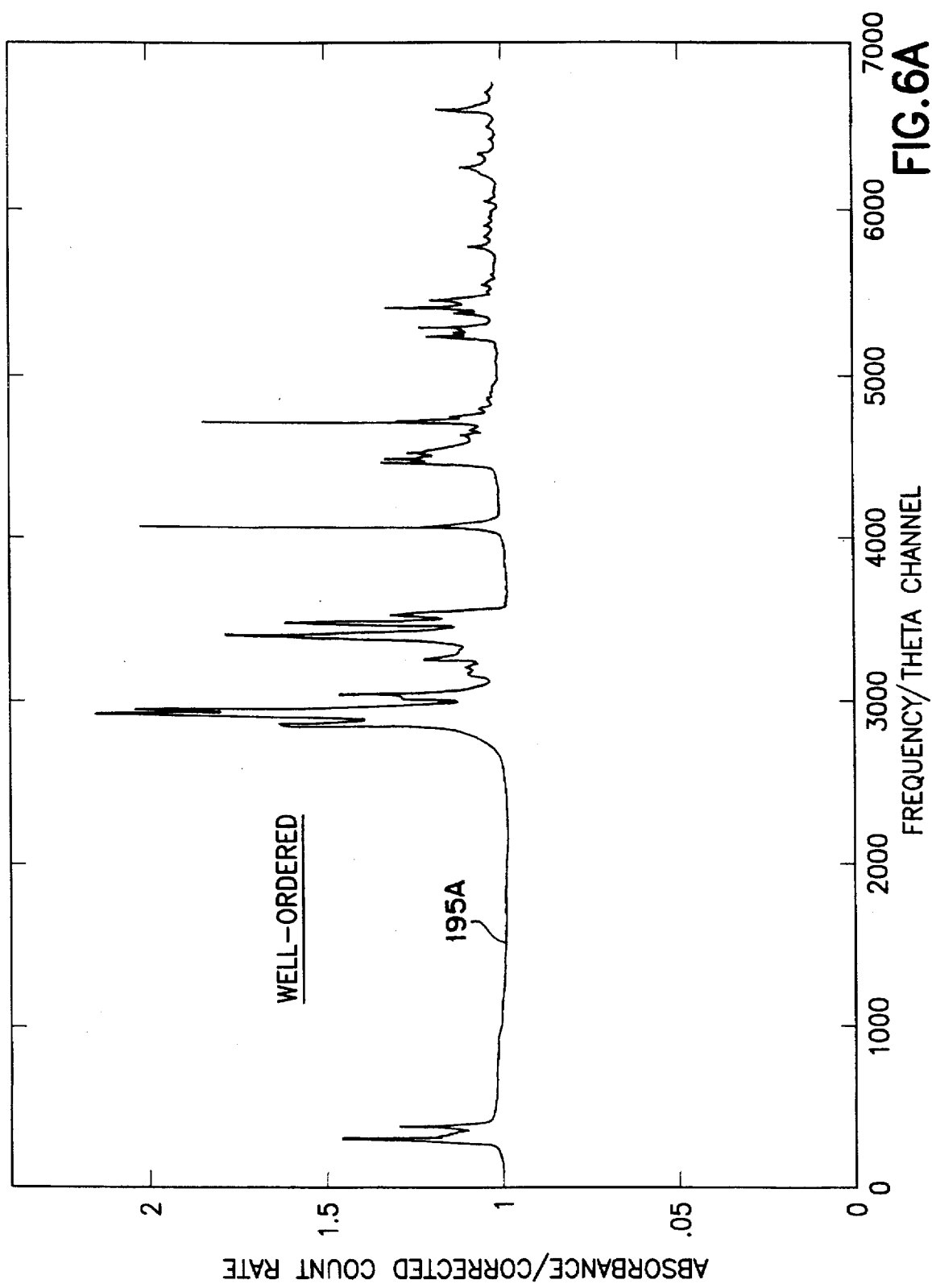

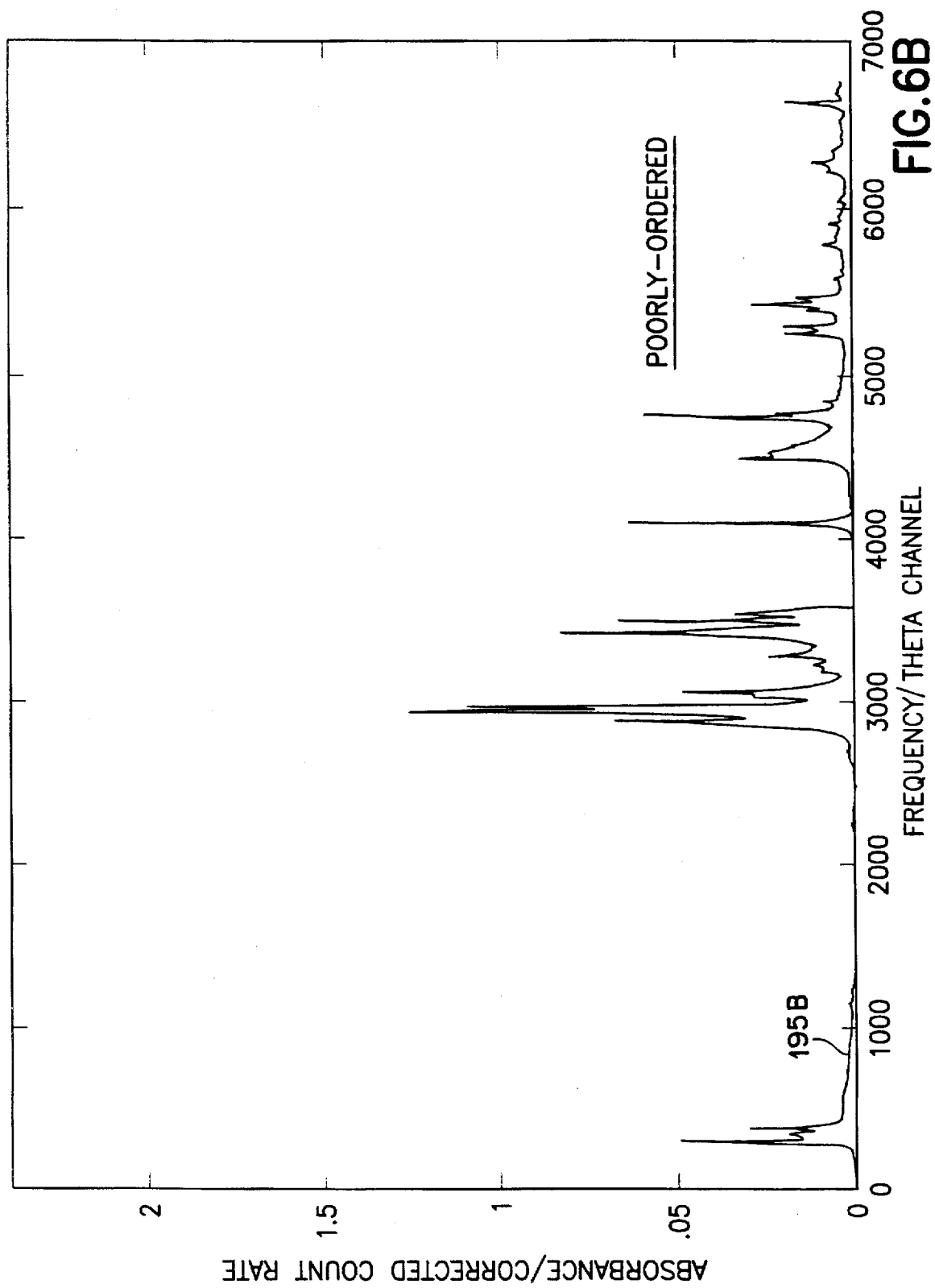

METHOD FOR QUANTITATIVE ANALYSIS OF EARTH SAMPLES

This application is a continuation-in-part of application Ser. No. 07/999,077; filed Dec. 31, 1992 and abandoned upon filing of this application.

BACKGROUND OF THE INVENTION

The present invention relates generally to investigating earth formations traversed by a borehole. More particularly, the invention relates to methods and apparatus for determining the mineralogy of a formation surrounding a borehole.

The mineralogy of an earth formation surrounding a borehole is valuable to determining whether it is feasible and cost efficient to produce hydrocarbons from the borehole in question. The identification of clays in the borehole is of particular importance. For example, it is known that smectite clays, if present as a minimum percentage of the formation composition may react with borehole mud by swelling and blocking pores through which hydrocarbons flow. Therefore, if smectite is present above the minimum level, it may be prudent to consider alternatives before incurring expense associated with producing hydrocarbons from the borehole. Similarly, clay minerals can conduct electricity and thus complicate the interpretation of electric logs.

In addition to providing clay content information, mineralogy of a formation also provides information indicating the presence of the other minerals in the formation. This information is useful in a number of ways. For example, some minerals make drilling more difficult and depending on which types of minerals are present in a formation, the costs and difficulties can be determined and compensated for prior to drilling a well through that formation.

Two basic techniques are used in the oil industry to perform quantitative mineral analysis of an earth formation. In both techniques, core samples are extracted from the borehole and are used to represent the formation at different depths. The first type of core analysis is performed by Fourier Transform Infrared (FTIR) spectroscopy. Typically, a portion of the core sample is ground up and added to a carrier such as potassium bromide (KBr). The mixture is then formed into a pellet through a series of grinding and dispersing steps. The pellet is pressed and weighed to account for lost material. Finally, the pellets are irradiated with infrared radiation in an FTIR spectrometer and a spectral response signal is obtained representative of the infrared radiation absorbed by the sample. The frequency and amplitude of each characteristic spectral response can be obtained. Comparison is made in the spectrum for the sample with spectra for standard minerals to determine a quantitative measure of the minerals in each sample. A typical FTIR core analysis is described in U.S. Pat. No. 4,839,516 to Freeman et al. and assigned to Western Atlas International, Inc.

The second type of core analysis commonly used in the oil industry is known as X-ray diffraction or "XRD." In accordance with this technique, a sample is crushed as in the FTIR analysis. A portion of the crushed sample is scanned using an X-ray device. The remainder of the sample is divided by size into a fine and coarse fraction and the fine fraction is mounted and run through a series of steps. After each step, an X-ray scan is performed and the scans are compared to determine the mineralogical content of the sample. This method is time-consuming and requires highly trained personnel to carry out. It requires from several hours to days to complete and is correspondingly expensive. A typical XRD procedure is described in published U.K. Patent Application No. 2,225,110.

Neither the FTIR technique nor the X-ray diffraction technique alone adequately provides sufficient data to make precise determinations as to mineralogical content of an earth formation traversed by a borehole. For some samples, one technique may provide inaccurate results for a particular mineral or even miss that mineral completely. That same mineral may be accurately characterized by the other technique. The present invention improves the accuracy of mineralogical analysis performed on the formation sample.

SUMMARY OF THE INVENTION

The present invention provides methods and apparatus for quantitatively analyzing core samples to determine the mineralogical composition of an earth formation traversed by a borehole. The invention overcomes many of the inadequacies of the prior art FTIR analysis and XRD analysis when performed independently. It overcomes these inadequacies by combining the two techniques to provide a single integrated spectrum from which a final mineralogy estimation can be made. Upon processing the integrated spectrum, it is possible to choose mineral estimates or combinations of estimates to yield the most accurate final mineralogical composition for the sample. In addition, the invention improves the results obtained by performing XRD analysis and FTIR analysis independently.

In addition, improved techniques for performing the FTIR and XRD techniques are implemented in arriving at the integrated spectrum, in accordance with the invention. Typically, once the sample is crushed and reduced to particles of a particular size, some of the sample is reserved for X-ray diffraction analysis while another portion is set aside for FTIR analysis. In one embodiment, the XRD portion of the sample is again split into two parts. The first part is run through a series of steps including: submersing a portion of the earth sample in a divalent cation solution causing a cation exchange reaction to replace a naturally occurring bond forming element between sample particles with a known bond forming element to standardize adsorbed cation state of clay minerals within the portion of the earth sample; spray drying a portion of the earth sample to randomly orient the particles of the sample; exposing the spray dried portion of the sample to a water replacement environment causing the replacement of varying amounts of interlayer water in clay layers to standardize the degree of swelling in clay minerals within the spray dried portion of the sample; and performing an X-ray diffraction scan of the sample to obtain an X-ray diffraction spectrum. The second portion of the sample set aside for X-ray diffraction analysis is run through the same steps except that it is combined with an internal standard, typically corundum, at the start. A number of correction steps are then performed on both X-ray diffraction spectra. The first spectrum is further adjusted in accordance with the known corundum peaks in the second spectrum to provide a corrected XRD spectrum.

A regression analysis can be performed on the corrected XRD spectrum with respect to a library of mineral standards using a linear combination of the spectrum in the standards set to provide the mineralogy of the sample.

The FTIR analysis also requires the performance of a series of steps on a portion of the earth sample set aside for FTIR analysis. These steps preferably include: dispersing the sample in a carrier using a mixer mill; evacuating the carrier plus earth sample in an evacuation oven; converting the sample into pellet form; and removing surface water from the sample in a vacuum oven. After these steps have been performed, the pellet is scanned using an FTIR spectrometer to provide an FTIR spectrum.

As with the X-ray diffraction technique described above, a regression analysis can be performed on the FTIR spectrum against a library of mineral standards to provide the mineralogy of the sample.

The present invention provides for integration of the XRD and FTIR spectra. In this case the XRD spectrum is combined with the FTIR spectrum prior to regression analysis. In order to optimize the determination of mineral quantities from the FTIR/XRD (FX) spectrum, weighting factors can be applied to each of the FTIR and XRD spectra. These weighting factors can be determined from a comparison of the quantities determined from the spectra of the standard minerals in the library with the known quantities of the standard minerals used to obtain the library. Once the FTIR spectrum is integrated with the XRD spectrum, the integrated FX spectrum is regressed against a library of FX spectra of standard minerals to obtain the mineralogy of the sample.

It is an object of the present invention to provide improved techniques for performing X-ray diffraction analysis and FTIR analysis of an earth sample for the purpose of providing more accurate estimations of the mineralogical composition of a particular earth sample.

It is a further object of the invention to provide a technique for integrating an XRD spectrum with an FTIR spectrum resulting in an integrated spectrum from which a resulting mineralogical composition of a sample can be determined.

It is yet a further object of this invention to provide a technique for quantitative analysis of the mineralogical composition of a sample using an entire FTIR-XRD (FX) spectrum without focusing on any one particular peak in the spectrum.

Another object of the invention is to implement a constrained spectral processing in both the FTIR and XRD analysis to further improve the results rendered by these techniques.

By achieving the objects of the invention, an appropriate production strategy for a particular borehole can be devised including a determination of the particular drilling and completion fluids used, the flow requirements, an appropriate acidizing technique, as well as a correction of a variety of logs obtained from logging tools run through the borehole.

BRIEF DESCRIPTION OF THE DRAWINGS

Additional objects and features of the invention will become more apparent upon consideration of the following detailed description of the invention when taken in conjunction with the accompanying figures:

FIG. 6A is an integrated FTIR-XRD (FX) spectrum for well-ordered kaolinite, and FIG. 6B is an FX spectrum for poorly-ordered kaolinite.

DESCRIPTION OF THE PREFERRED EMBODIMENT

The present invention is primarily directed to analysis of core samples obtained from boreholes extracted during oil and gas exploration and production. The core samples may be taken during the exploratory process prior to production of hydrocarbons or from an infill well. A core sample is typically a few inches diameter and up to several feet long. It is common to extract a smaller sample from the sample taken from the well for analysis. These smaller samples are frequently referred to as "plugs." The plugs are commonly 1" in diameter and 1½" long. Samples may also be taken from the side walls of the borehole and are usually similar in size to a plug. In addition to analysis of core samples, drill cuttings resulting from the drilling process can also be analyzed. For the purpose of this application, the term "core samples" will be used to include any earth sample taken for analysis.

Before the techniques of the present invention are applied, the sample to be analyzed is cleaned to remove hydrocarbons which may be present. Various core cleaning methods and combinations of methods such as toluene solvent extraction or $CO_2$ cleaning may be used. These cleaning techniques are well known in the art and will not be described here.

Figure 1A:
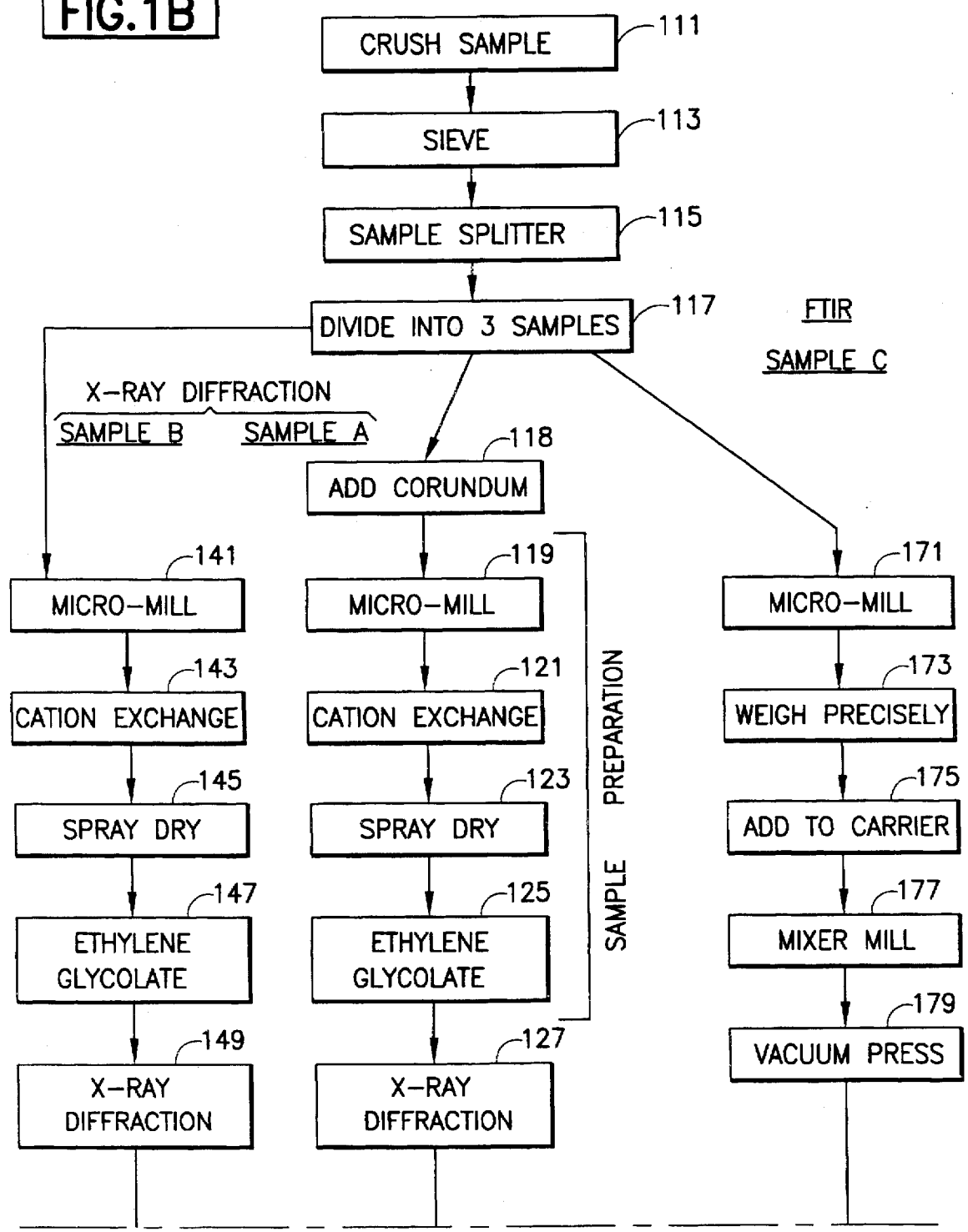
FIG. 1 is a flowchart of the steps performed in accordance with the present invention.
Figure 1B:
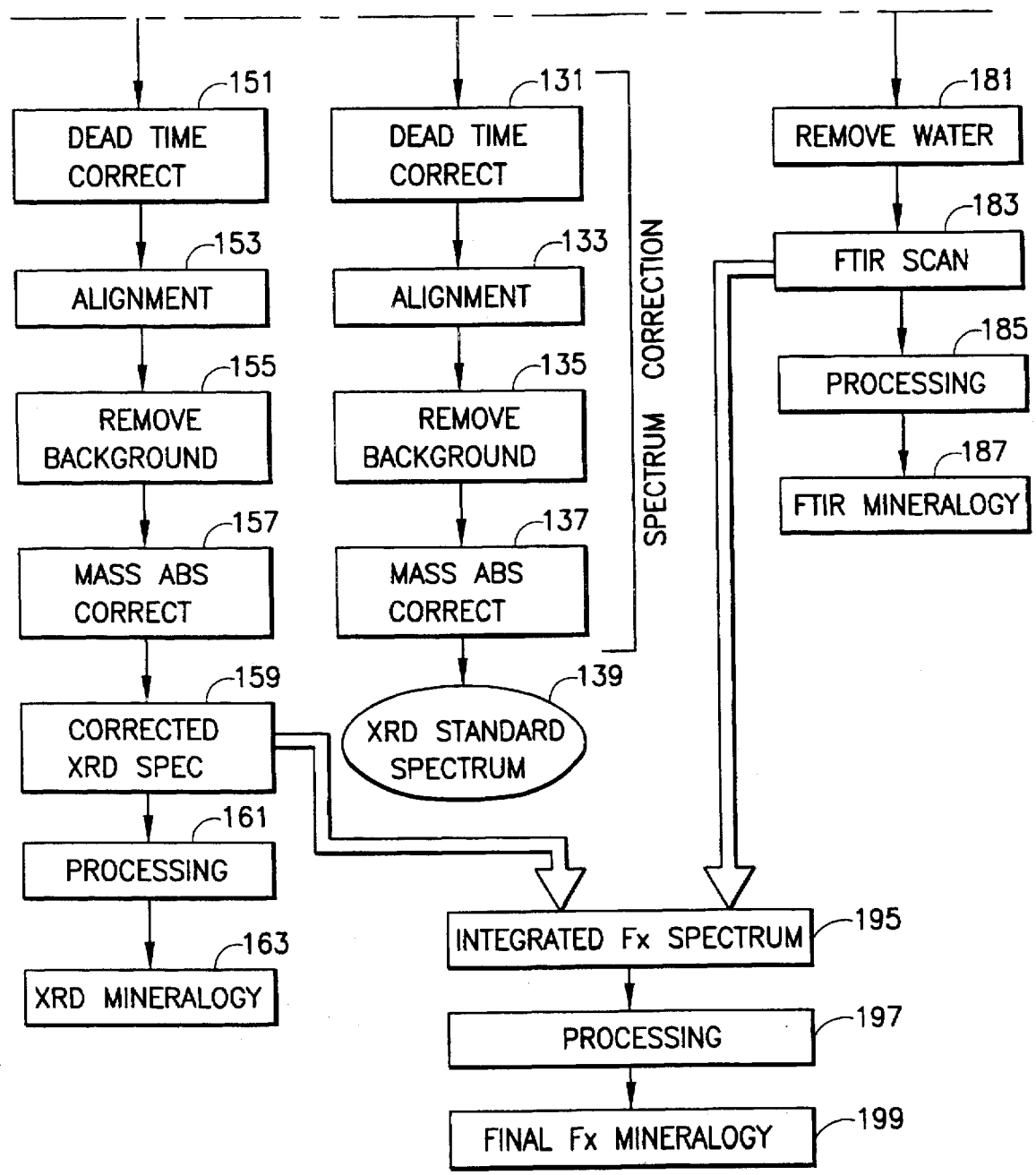

FIG. 1 is a flow chart of the method for performing mineralogical analysis according to one embodiment of the present invention. Once the sample has been cleaned, it is crushed 111 using a mortar and pestle or some other apparatus for crushing a sample. The crushed sample is then sieved 113 to ensure that particles are less than 500 micrometers. It has been found that the removal and recrushing of particles greater than approximately 500 microns is preferable. After the particles are sieved 113, they are deposited in a micro sample splitter 115 which divides the sieved sample into a number of homogeneous portions.

In accordance with the invention, sample splitter 115 provides three separate sample portions 117 for analysis. Two of these portions are used to provide the X-ray diffraction analysis and the third portion is used to provide the FTIR analysis.

Preparation of the first two samples for X-ray diffraction analysis will now be described. The first sample portion, referred to as sample A, is taken from sample splitter 115 and mixed with a corundum additive. The corundum produces peaks in the XRD spectral pattern which are used as an "internal standard" for aligning the spectra. This operation will be discussed in detail below. Sample A is then placed in a micronizing mill 119, typically produced by McCrone Research Associates, Ltd. of London, England. The micronizing mill reduces the size of the particles to less than 2.5 micrometers in diameter. It has been found that this size provides better random orientation of the particles during the later steps of the X-ray diffraction analysis.

The sample from the micronizing mill is treated with a divalent cation ($Ca^{2+}$) solution 121 which replaces exchangeable cations. Excess solution is removed from the sample by a deionized water rinse. The reason for treating the sample with the divalent cation solution is that natural clay minerals may contain a combination of adsorbed cations such as $Na^+$, $Ca^{2+}$, $Mg^{2+}$, etc. The variety of adsorbed cations in the clay causes the individual elemental bonding structures of the swelling clays to vary in size. By treating the sample with a divalent cation solution, the varying bond elements between sample particles are replaced with a chosen bond forming element, in this case $Ca^{2+}$, at each bond to minimize size variability. It should be understood that other cation solutions could be easily used in place of one made with $Ca^{2+}$.

The sample which is now made up of particles with uniform elemental structure size is mixed with a binder and spray dried 123. A Glatt spray dryer manufactured by Glatt Air Techniques, Inc. of Ramsey, N.J. has proven to be effective for this purpose with a typical binder of polyvinyl alcohol. The spray dryer is employed to achieve a random orientation pattern of mineral particles when the sample is later scanned by an X-ray beam. This random orientation achieves a reproducible non-biased X-ray pattern which is critical to achieving accurate results.

Quantitative analysis is practical only if the minerals are all either perfectly oriented or randomly oriented. Some minerals are blocky in shape and do not preferentially orient themselves when poured in a sample cup. Other minerals, however, are platy like micas and clay minerals and these show a strong tendency to lie flat like playing cards. If all the platy minerals lie perfectly flat, the sample would be perfectly oriented. The spray drying technique described above achieves random orientation by creating large spherical droplets of binder and mineral particles of less than approximately 2.5 micrometers in diameter.

Figure 2:
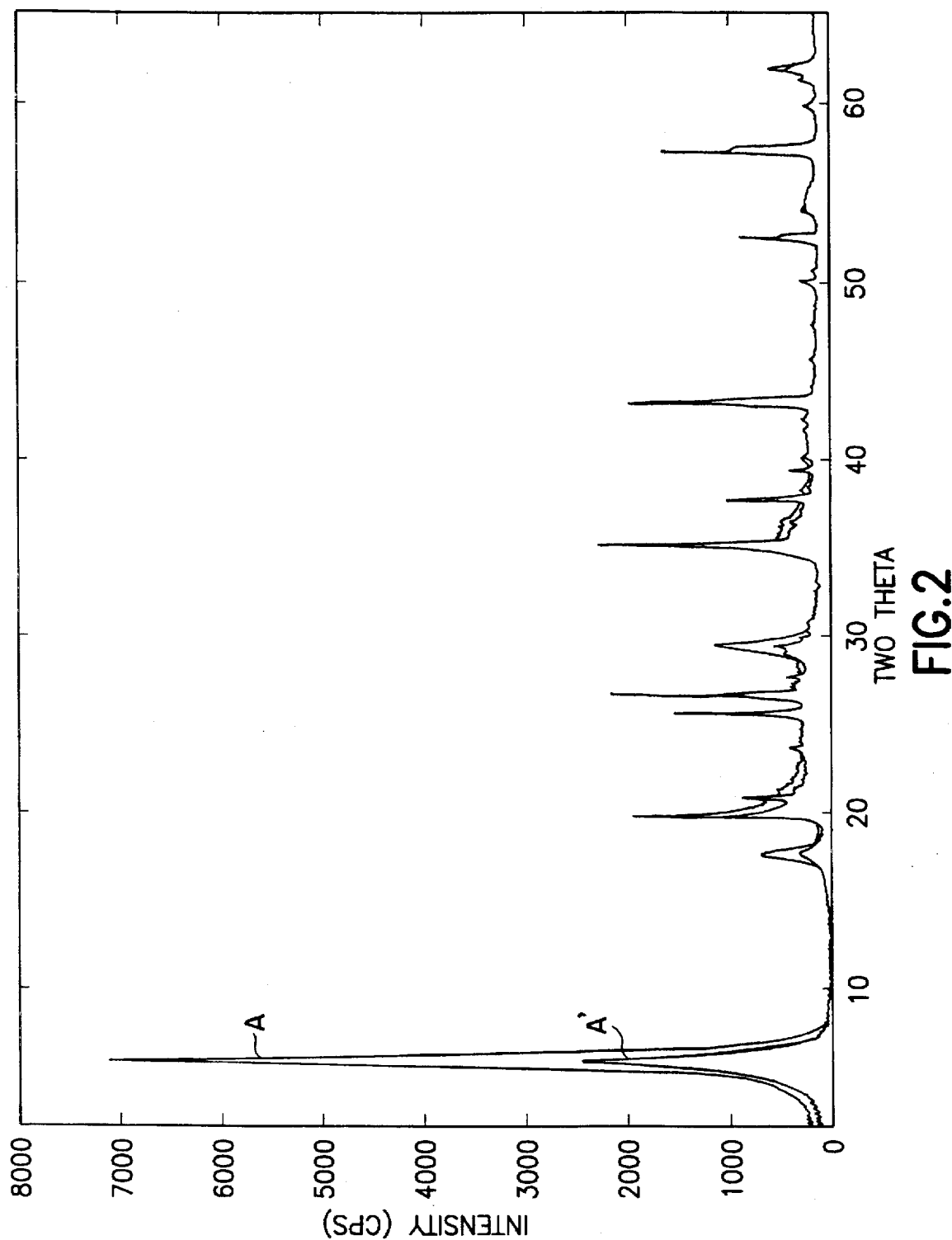
FIG. 2 compares XRD patterns for a conventional random pattern mount and for a truly random spray dried mount for the clay mineral montmorillonite.

FIG. 2 is a comparison between X-ray diffraction patterns for a conventional "random" powder mount and for a truly random spray dried mount for the clay mineral montmorillonite. The spectra are shown as a function of intensity measured in counts per second (CPS) versus the angle of the X-ray device (2 θ). The spray dried technique used in steps 123 and 145 produces truly random mounting of the sample. In FIG. 2, it can be seen that peak A at about 5° on the 2 θ axis is nearly a factor of three times higher in the conventional "random" mount than in the newly developed mount using the spray dried technique represented by peak A'. This peak increases quickly with preferred orientation and FIG. 2 illustrates that the conventional mount is far from truly random in orientation. In addition to the discrepancy between peak A and A', it is clear that at many of the other peaks in the figure as well as the points along the general curve, the conventional "random" powder mount produces a spectrum which is inaccurate.

The spray dried sample is placed in a dessicator in an oven with an ethylene glycol atmosphere at 125° C. for at least 18 hours. Glycolation is essential for accurate quantification of the clay mineral smectite and smectite layers in mixed-layer clays. The ethylene glycol replaces the varying amounts of interlayer water in the smectite layers and forces these layers to have a constant spacing. This step produces a similar result to the cation exchange described in step 121: minimizing structure size variability.

An X-ray diffraction scan 127 is now performed on the sample. This is done by placing the sample in a sample cup and scanning with an X-ray diffraction scanner between 2° and 65° on a 2 θ scale. The sample spectrum is corrected through the performance of a number of procedures. First, a dead time correction 131 is applied to the spectrum. This correction takes into account the detector response with respect to the incoming X-rays. The spectrum is processed by an empirically-derived correction that is well known in the industry to eliminate the effect of dead time operation.

Alignment 133 is the next step which is applied to the spectrum to correct it to its actual position. Alignment takes into account that the exact position of the sample cup is not known or reproducible. Therefore, the initial 2 θ position varies for each sample. To correct this, the 2 θ position of the corundum peaks in sample A are aligned to match known values for corundum. In other words, the entire spectrum is shifted to the left or right to line up the corundum peaks in the sample spectrum with the known corundum 2 θ values.

Figure 3:
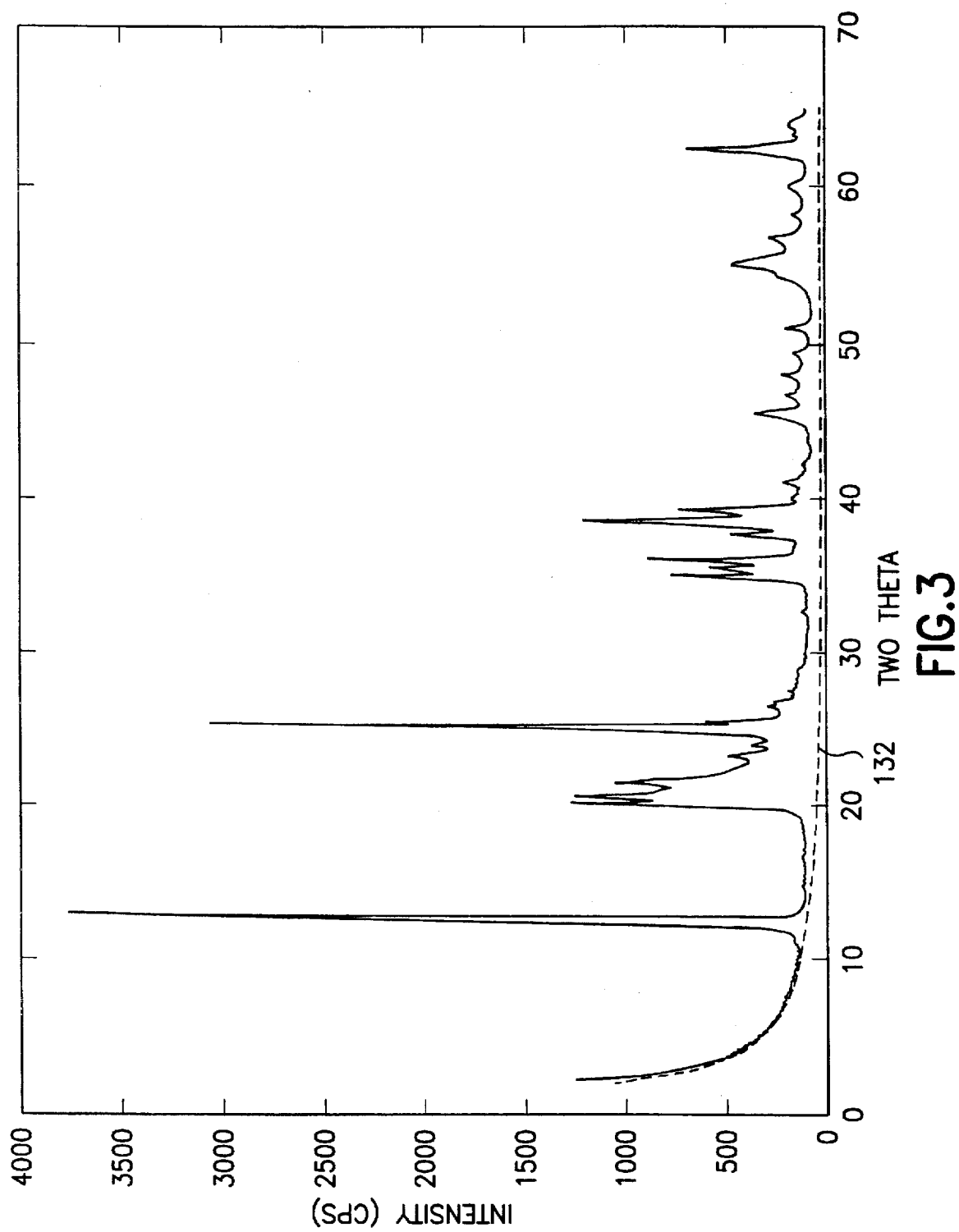
FIG. 3 is a randomly oriented XRD spectrum for uncorrected spray dried kaolinite and the background pattern.

Background noise is a function of the angle of the X-ray diffraction apparatus and is especially high at low angles. This is because when the X-ray source and receiver lie close to the horizontal position, some of the emission from the source is directed into the receiver without first diffracting through the sample. This signal obscures critical diffraction peaks for the clay minerals. An example of background noise in a spectrum is shown in FIG. 3 wherein a randomly oriented X-ray diffraction pattern for uncorrected spray dried kaolinite is superimposed on a background pattern. The background pattern is illustrated by the dotted line 132 and is removed from the spectrum in steps 135 and 155. A background spectrum can be constructed from the analysis of multiple standards which takes into account the background noise. This background spectrum is subtracted from the sample and standard spectra to remove the background noise.

Finally, the spectrum is corrected for the sample's mass absorption coefficient 137. Different minerals absorb X-rays with different efficiency rates. The result is to variably reduce the quantity of reflected X-rays reaching the detector. The mass absorption coefficient accounts for the variability of different minerals to absorb X-rays as a function of chemical composition. This procedure also corrects for variable droplet density of spray dried spheres in the sample container. To accomplish this correction, a gain correction factor is applied such that the corundum peak heights of the mixture match those of spray dried pure corundum adjusted for the corundum content of the mixture (50% in this case).

A second sample, sample B, is run through the same series of steps as the first sample. The only difference is that corundum, which is used as an internal standard in the first sample, is not added to the second sample. Therefore, the second sample is a pure representation of the earth formation which is being analyzed. As with the first sample, the second sample is prepared by placing it in a micronizing mill 141, performing a cation exchange 143, spray drying 145, and exposing it to an ethylene glycol environment 147 in an oven. An X-ray diffraction scan is performed in step 149. The resulting spectrum is then run through a series of correction steps. Dead time correction 151 is the same as that applied in step 131 for the first sample.

Alignment 153 is a critical step in the X-ray diffraction analysis of the present invention. Alignment is achieved by comparing the peaks of the spectrum from the second sample with the previously corrected peaks of the first sample spectrum. The alignment step 153 shifts the spectrum to a true position for the sample. As with sample A, the background noise for sample B is removed 155 and the mass absorption coefficient for the sample is corrected 157. A corrected XRD spectrum 159 for the sample results.

Figure 4:
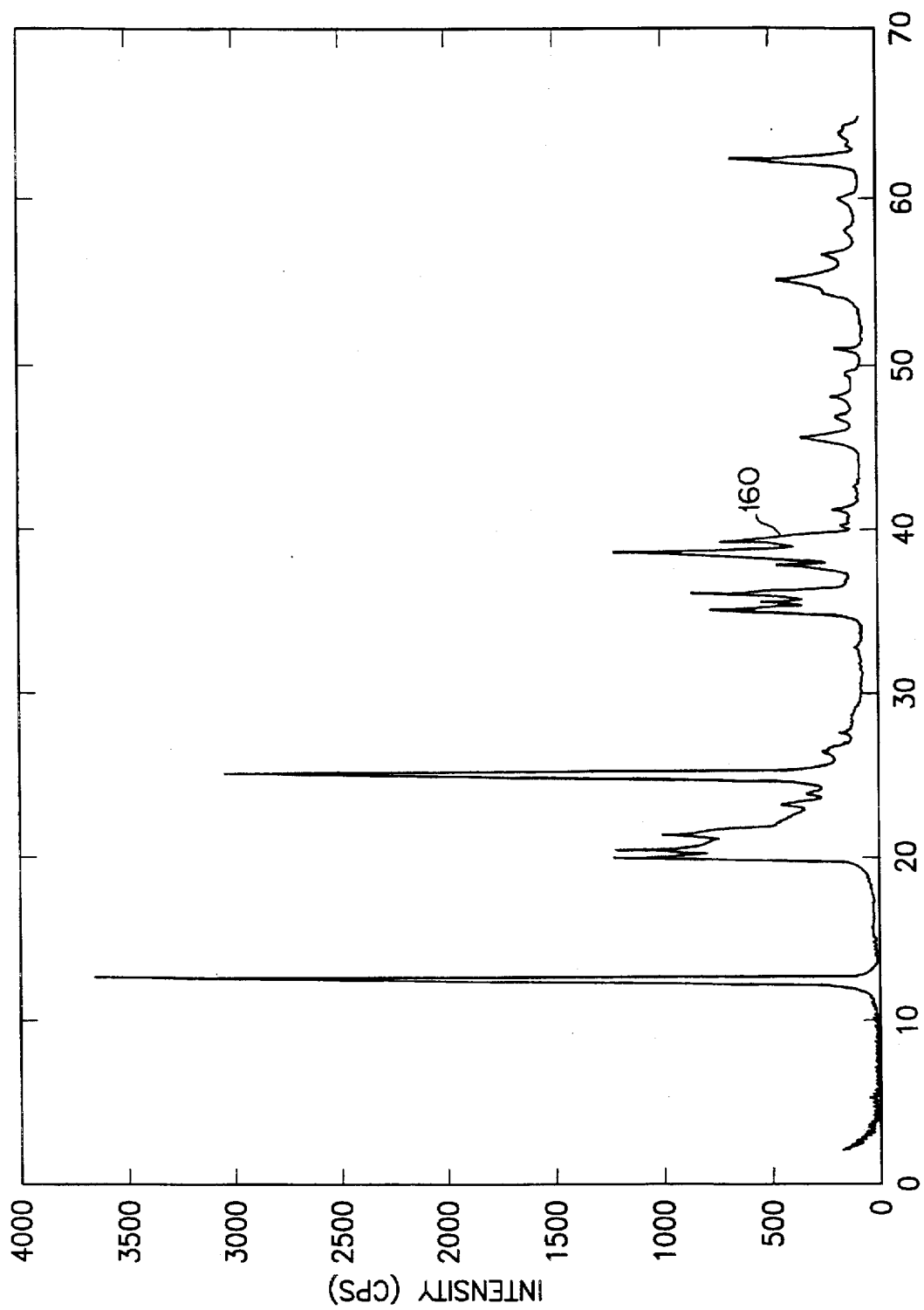
FIG. 4 is a final corrected XRD spectral pattern for the mineral kaolinite.

FIG. 4 shows the final corrected pattern 160 for the mineral kaolinite. As can be seen from this figure, the background signal has been removed and the left portion of the spectrum has been reduced along the intensity axis. Note that the remaining signal is composed of peaks at discrete angles and a low-level residual signal spread over the entire spectrum.

If an independent XRD analysis is desired, the corrected XRD spectrum is regressed against a library of XRD spectra of characterized mineral standards. The library includes multiple samples for each mineral of varying structure.

Some minerals do not exhibit structural or chemical variability. Therefore, each of these minerals can be represented by one spectrum. Other minerals, such as kaolinite exist as a number of distinguishable species. For these minerals, the standards set includes more than one spectrum. The entire spectra of the sample and standards from 2° to 65° on the 2 θ scale, is used in the processing. Data processing such as smoothing to remove noise may occur at this point. Such smoothing, which may involve a low band pass filter operation, is known in the art.

The final XRD mineralogy 163 is determined by regression analysis using a constrained spectral processing program 161. The XRD spectrum is essentially a dataset comprising a series of values. The position of each datum in the series corresponds to its 2 θ value and the magnitude of each datum corresponds to the intensity of the X-ray diffraction signal (counts per second) for that 2 θ value. For mineralogical analysis, XRD spectra (datasets) are obtained for a series of standard minerals so as to define a library from which the composition of an unknown sample can be inferred. The datasets comprising the spectra can be analyzed using statistical methods; in the present case the data set comprising the unknown mineral is regressed against the library datasets. Regression of data against a library of known data is a well-known method of analyzing this type of data to calculate unknown quantities. The processing is performed on the sample spectrum data set as a linear combination of the spectral data in the standards set as described in *Solving Least Squares Problems* by Charles L. Lawson and Richard Hanson, Prentice-Hall (1974). However, certain constraints must be placed on the analysis so that is does not give impossible results arising from the nature of the analysis. In the present case, the constraint is that the minimum amount of a mineral possible is 0%, it cannot be negative. One method to perform regression analysis constrained in this manner is to perform nonnegative least squares analysis on the data. An example of constrained spectral processing using non-negative least squares processing can be found in 1993 Society of Core Analysts Conference, Paper No. 9308, "Quantitative Mineral Analysis by Fourier Transform Infrared Spectroscopy". Non-negative least squares processing has been used extensively in the area of inverse problem solving. This processing technique is applied to the FTIR and XRD analysis used in the present invention to constrain the analysis to give mineral qualities of not less than 0% and to avoid unwanted crosstalk between highly correlated mineral standard spectra. The avoidance of this crosstalk between standard spectra is useful in allowing more accurate results to be achieved in accordance with the present invention. Since non-negative least squares processing is known from the area of inverse problem solving, it will not be described in detail here.

Attention is now turned to the third sample, sample C, used for FTIR analysis. Sample C is ground under alcohol in a micronizing mill 171. Preferably, the micronizing mill is run for approximately 30 minutes to reduce the grain size of the particles in the sample to less than 2.5 micrometers in diameter. This size requirement is essential for the homogeneous distribution of sample when it is added to a carrier compound and to minimize light scattering during the FTIR scan.

The sample is taken from the micronizing mill 171 and the sample is weighed precisely. In addition, a carrier compound, typically potassium bromide (KBr), is also weighed precisely in step 173. It has been found that a Cahn microbalance provides the accuracy needed for weighing the sample and the carrier. The sample is then added to the carrier 175 and dispersed into the carrier using a Brinkmann Retsch mixer-mill manufactured by Retsch GMBH of Germany. The sample is removed from the mixer-mill and again weighed using the Cahn microbalance. The sample is transferred to an evacuable die and placed under a vacuum in a press 179 where the sample is converted to pellet form. From the vacuum press the pellet is transferred to a vacuum-oven to remove surface water 181.

Figure 5A:
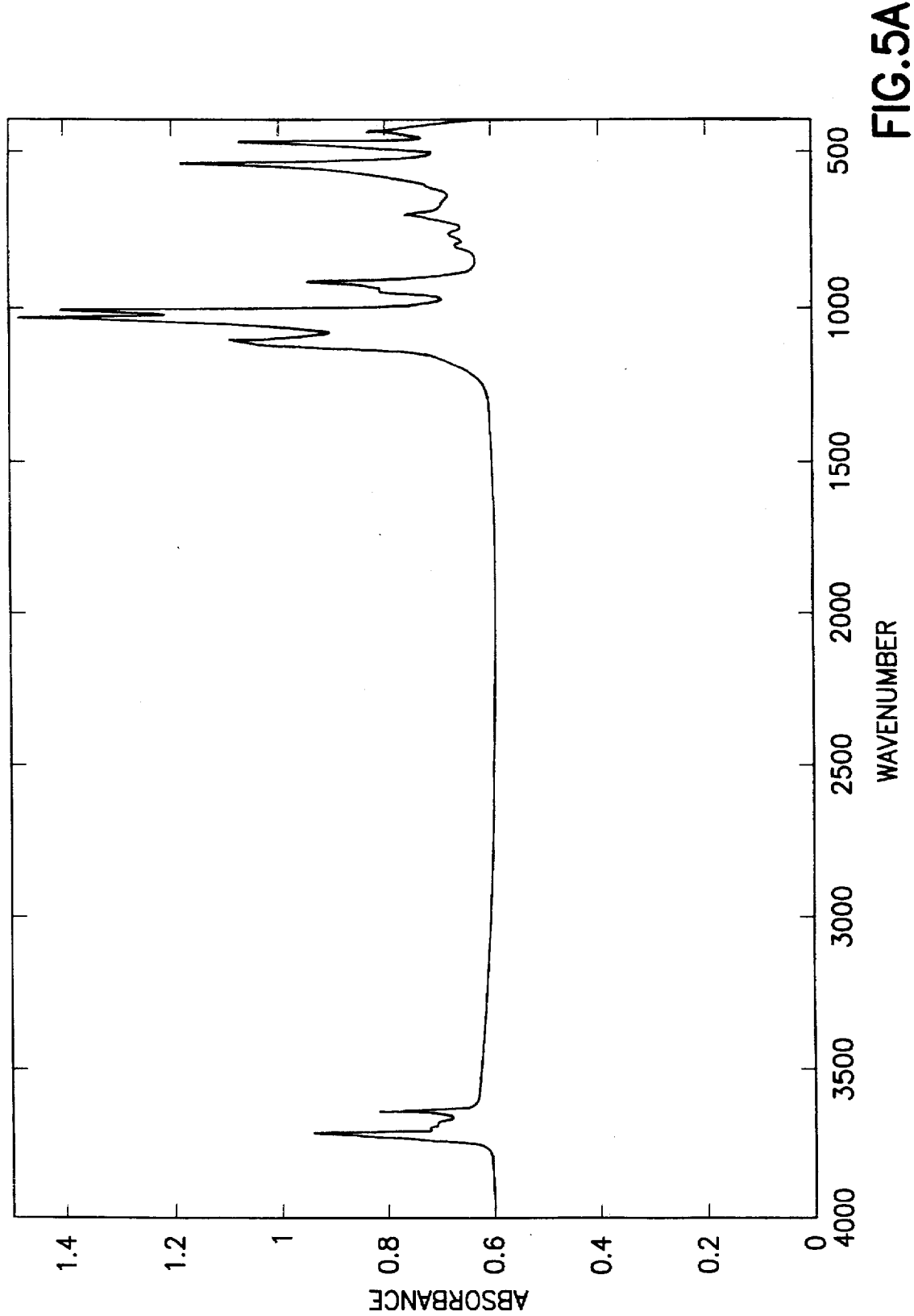
FIG. 5A is an FTIR spectra for well-ordered kaolinite.
Figure 5B:
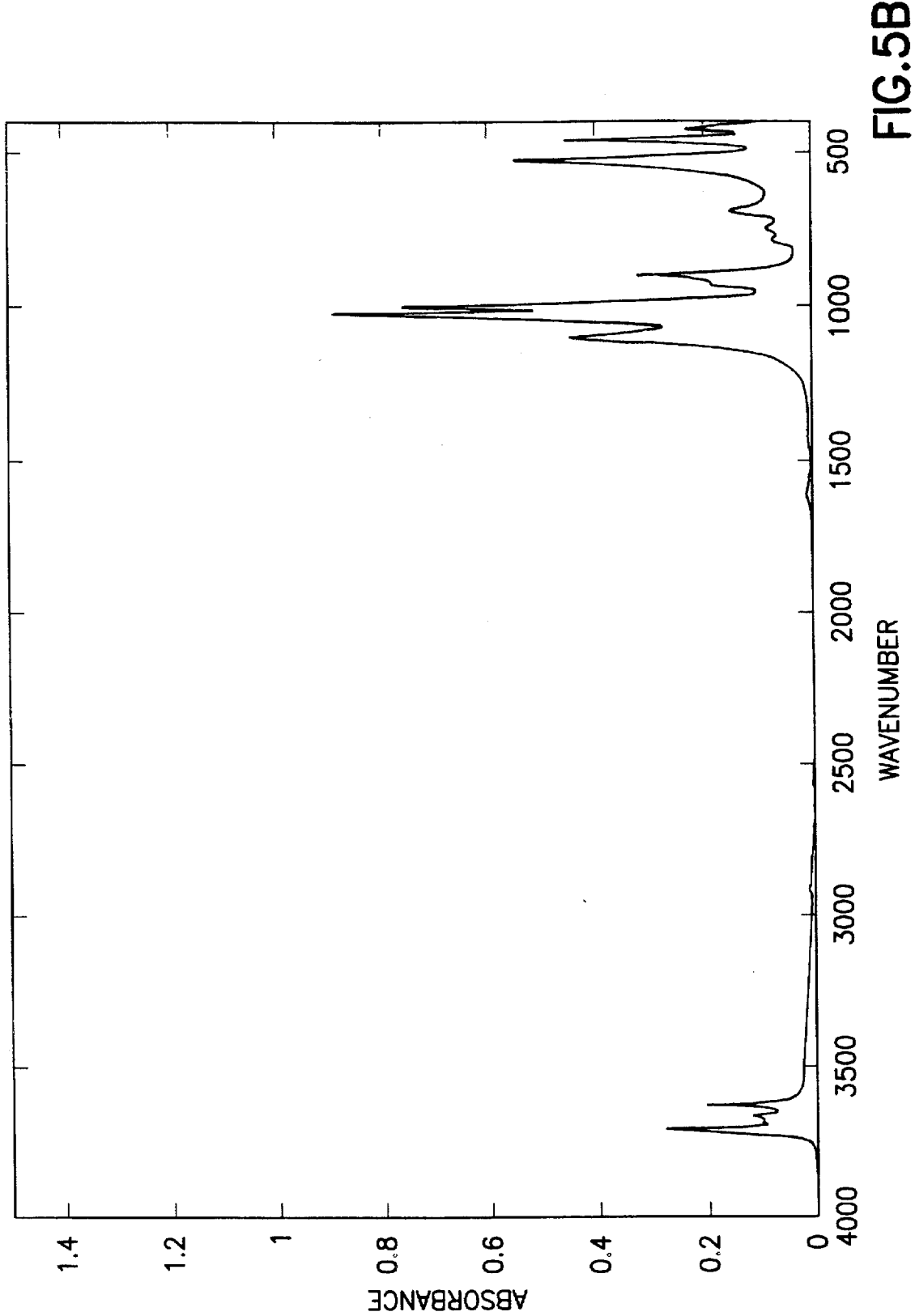
FIG. 5B is an FTIR spectra for poorly-ordered kaolinite.

An FTIR spectrum for the sample is obtained by scanning the sample in an FTIR spectrometer 183. Typically, 25 scans are performed in the range of 4000–400 $cm^{-1}$ at a resolution of 4 $cm^{-1}$. The spectrometer, typically manufactured by Perkin-Elmer of Norwalk, Conn., ratios the transmitted intensity of the sample to that of air or a blank pellet and converts to net absorbance. FIG. 5A shows an FTIR absorbance spectrum for well-ordered kaolinite and FIG. 5B shows an FTIR spectrum for poorly-ordered kaolinite. FIG. 5A is offset by 0.6 along the absorbance axis for convenience so that it is easier to examine the individual spectra. Although FIGS. 5A and 5B appear very similar, they do contain differences which are critical to an accurate analysis. For example, in the group of peaks occurring at approximately 3600–3700 on the wavenumber axis, the poorly-ordered kaolinite (5B) includes a small peak between the two larger peaks whereas the well-ordered kaolinite (5A) does not include this peak.

A blank carrier pellet of KBr without rock sample is also prepared in accordance with steps 177, 179, and 181. The carrier pellet is then scanned in the same manner as the sample pellet in step 183. The carrier spectrum obtained from the FTIR scan can be used in two ways to correct the sample spectrum. First, it can merely be subtracted to eliminate the carrier from the sample spectrum. A second and preferred technique is to also incorporate the carrier spectrum in the standards set for use in steps 185 and 187 described below. This technique has been found to provide better results.

If an independent FTIR analysis is desired, the next step is to perform regression analysis on the sample spectrum. A library of FTIR spectra from characterized mineral standards of the same minerals that are X-rayed, has been collected. The library includes multiple samples for each mineral with varying structure or chemistry just like the library of standards for X-ray diffraction analysis. Some of the minerals do not exhibit structural or chemical variability and are therefore represented in the standard set by a single spectrum. Other minerals, such as kaolinite, exist in the form of a number of distinguishable species. For these minerals, the standards set includes more than one spectrum. The entire absorbance spectra (4000–400 $cm^{-1}$) of the sample and standards, excluding areas of variable contamination, are used in the processing step. The sample spectra are regressed against the library of mineral standards and the final FTIR mineralogy 187 is determined by constrained spectral processing 185 such as non-negative least squares processing as described above in relation to analysis of XRD spectra.

Although the X-ray diffraction and the FTIR techniques discussed above may be practiced independently of one another to obtain improved results over the prior art, the present invention provides for integrating the two techniques into a single spectrum for final processing. The integrated spectrum 195 is comprised of the corrected XRD spectrum obtained from step 159 and the FTIR spectrum obtained from the FTIR scan in step 183.

The integrated FX spectrum is essentially a dataset formed from the XRD and FTIR datasets. The FX dataset retains values indicative of the magnitudes from each individual dataset although these might not be exactly the same in the FX dataset as will be described below. The integrated dataset must also retain the relationship from the data position in the series for the individual spectrum datasets. In its simplest form, the FX spectrum dataset comprises all of the data from one spectrum followed by all of the data from the other spectrum as is shown in the spectrum plot of FIG. 6. However, the integrated spectrum dataset is by no means restricted in this. Data from the two original datasets (spectra) can be interspersed in the integrated dataset provided that the series position relationship between data originating in one set is maintained in the integrated set.

FIG. 6 shows an FX spectra for well ordered kaolinite (6A) and poorly ordered kaolinite (6B). The well ordered kaolinite spectrum is offset by 1.0 along the absorbance/corrected count rate axis for convenience so that it is easier to examine the individual spectra. These spectra are formed from an FTIR portion (FIG. 5) which is between 0 and approximately 3500 on the Frequency axis and an XRD portion (FIG. 4) which is between approximately 3500 and 7000 on the Frequency axis. It should be understood that the physical representation of the integrated FX spectrum can take on many forms. For example, the order of the FTIR and XRD spectra is not critical. The XRD spectrum could be placed first with the FTIR spectrum appended thereto.

The integration of the XRD and FTIR spectra is accomplished by assigning a weighting factor to each of the FTIR and XRD spectra.

The area beneath the peaks of the spectra (or the sum of the magnitude values in the data series comprising the spectra) is what is analyzed, in effect, to obtain the mineralogical information. When integrating the XRD and FTIR spectra, it is important that the contribution of each to the total area of the FX spectrum is optimized. Put simply, if the area contribution of say the XRD spectrum to the FX spectrum is significantly greater than that of the FTIR spectrum, the contribution of that spectrum to the final analysis will be proportionally greater as will be the errors and deficiencies inherent in that spectrum. This problem can be avoided by weighting the data contributed to the FX spectrum dataset. One very simple method of weighting is the to ensure that the area enclosed by each spectrum is the same before integrating, i.e. the total of the magnitude values for each series is the same. In the example of FIG. 6 the magnitude of the XRD spectral data is multiplied by a factor of 0.000286 such that the area under the XRD spectrum is substantially the same as that under the FTIR spectrum. The weighting factor in this case is easily derived from a comparison of the areas under each spectrum.

It is not essential that weighting be applied uniformly to a whole spectrum. It has been found that certain parts of a spectrum, either XRD or FITR, contain proportionally more mineralogical information than others. Consequently, data within a spectral dataset can be weighted to optimize the contribution of the data containing the useful information. An example of this can be found in *Applied Spectroscopy*, Vol. 47, No. 11, 1993, "Empirically Minimax Affine Mineralogy Estimates from Fourier Transform Infrared Spectrometry Using a Decimated Wavelet Basis". This general approach can be applied to individual spectra, both XRD and FTIR, or to the integrated spectrum.

The weighting factors are determined by comparing values determined from mineral contents from the spectra with known values of mineral contents when analyzing standards. These weights can then be applied to the unknown spectra.

As with the independent techniques of X-ray diffraction analysis and FTIR analysis, the integrated FX spectra 195 is regressed against a library of FX spectra constructed from the FX spectra of mineral standards. A constrained spectral processing technique 197 such as non-negative least squares is used to determine mineralogy as a linear combination of the FX spectra in the standards set as described above with respect to steps 161 and 185. The resulting final FX mineralogy 199 is obtained as a function of a combination of vibrational energy probed by FTIR and lattice spacing measured by XRD. The mineralogy, which is dependent on the assigned weighting for FTIR and XRD, is more accurate than that from either FTIR or XRD alone.

In general, to those skilled in the art to which this invention relates, many changes in construction and widely differing embodiments and applications of the present invention will suggest themselves without departing from the spirit and scope. For example, other constrained spectral processing techniques besides non-negative least squares could be used. In addition, the weighting factors used in the integration of the XRD and FTIR spectra may change depending on the sample being analyzed to optimize the accuracy of the results. Thus, the disclosures and descriptions herein are purely illustrative and are not intended to be in any sense limiting. The scope of the invention is set forth in the appended claims.

What is claimed is:

1. A method of analyzing the composition of an earth sample to determine the presence of particular minerals in the earth sample, comprising the steps of:

(a) obtaining an FTIR spectrum of the earth sample and creating a dataset therefrom;

(b) obtaining an XRD spectrum of the earth sample and creating a dataset therefrom;

(c) combining data from the datasets created from the FTIR spectrum and the XRD spectrum to define an integrated spectrum dataset for the earth sample;

(d) analysing the integrated spectrum dataset by performing regression analysis against a library of data obtained from standard spectra using a constrained spectral processing technique; and (e) determining a quantitative mineralogical composition of the sample from results obtained by the regression analysis; and wherein step (b) includes the steps of:

(i) reducing the earth sample into a fine powder of particles no more than substantially 2.5 microns in diameter;

(ii) disposing a first portion of the earth sample in a divalent cation solution causing a cation exchange reaction to replace a bond-forming element between sample particles with a chosen bond-forming element at each bond to minimize variability of adsorbed cation of clay minerals within the first portion of the earth sample;

(iii) spray drying the first portion of the earth sample to randomly orient the particles of the sample;

(iv) exposing the spray-dried portion of the earth sample to a water-replacement environment causing replacement of interlayer water in clay layers to minimize variability of interlayer spacing of clay minerals within the exposed portion of the earth sample;

(v) performing an XRD scan on the exposed portion of the earth sample to obtain an XRD spectrum for the sample including spectral peaks, representing various minerals;

(vi) adding an additive to a second portion of the earth sample to be used as an internal standard for comparison purposes;

(vii) repeating steps (ii)–(v) for the second portion; and (viii) determining the position of the additive peaks in the XRD spectrum of the second portion and determining an error between the determined position and height and the known position and height of XRD peaks and removing said error from the position and height of the peaks in the XRD spectrum of the first portion.

2. The method of claim 1 wherein the error corrected for is caused by background noise recorded during the XRD scan.

3. The method of claim 1 wherein the error corrected for is caused by machine limitations in performing the XRD scan.

4. The method of claim 1 wherein the error corrected for is a mass absorption coefficient for a sample mass.

5. The method of claim 1 wherein the earth sample is placed in a micronizing mill to obtain particle size less than substantially 2.5 microns.

6. The method of claim 1 wherein the water replacement environment is a dessicator with an ethylene glycol atmosphere.

7. The method of claim 1 wherein the X-ray diffraction scan of step (v) is conducted substantially between the angles of 2° and 65° on a 2 θ scale.

8. The method of claim 1 wherein the constrained spectral processing of step (d) is non-negative least squares regression of the data comprising the integrated dataset of the earth sample against the the library of data obtained from standard spectra.

9. The method of claim 1 wherein step (c) includes assigning a first weighting factor to the FTIR spectrum dataset and a second weighting factor to the XRD spectrum dataset prior to combining the two datasets.

10. The method of claim 1 wherein step (iii) is performed by mixing the earth sample with a binder material.

11. The method of claim 10 wherein the binder material is formed of water and polyvinyl alcohol.

12. The method of claim 1 wherein the additive is corundum.

13. The method of claim 12 wherein step (viii) comprises:

comparing the internal standard to known corundum data to correct for error in spectrum containing the internal standard; and aligning peaks and adjusting height in the sample XRD spectrum for the portion with a corrected internal standard.

14. The method of claim 1 wherein step (a) includes the steps of:

(i) reducing the earth sample into a fine powder of particles no more than substantially 2.5 microns in diameter;

(ii) dispersing the earth sample in a carrier using a mixer-mill;

(iii) converting the sample into pellet form;

(iv) removing surface water from the pellet in a vacuum-oven;

(v) performing an FTIR scan on the pellet to obtain an FTIR spectrum for the sample including spectral peaks representing various minerals;

(vi) repeating steps (iii)–(v) for a sample of only carrier to obtain an FTIR spectrum including spectral peaks representing the carrier only; and (vii) using the carrier FTIR spectrum to evaluate a contribution of the carrier to the sample FTIR spectrum.

15. The method of claim 14 wherein the scan of step (v) is substantially in the range of 4000–400 $cm^{-1}$.

16. The method of claim 14 wherein the carrier is potassium bromide (KBr).

* * * * *